US008628581B2

United States Patent
Zang et al.

(10) Patent No.: US 8,628,581 B2
(45) Date of Patent: Jan. 14, 2014

(54) CONICAL, THREADED SUBTALAR IMPLANT

(75) Inventors: Kerry Zang, Paradise Valley, AZ (US);
Shaher A. Ahmad, Plano, TX (US);
Lisa R. Thornhill, Dallas, TX (US)

(73) Assignee: OsteoMed LLC, Addison, TX (US)

( * ) Notice: Subject to any disclaimer, the term of this patent is extended or adjusted under 35 U.S.C. 154(b) by 1325 days.

(21) Appl. No.: 10/777,514

(22) Filed: Feb. 11, 2004

(65) Prior Publication Data

US 2005/0177165 A1    Aug. 11, 2005

(51) Int. Cl.
*A61F 2/42* (2006.01)
(52) U.S. Cl.
USPC .................. 623/21.18; 606/301; 606/321
(58) Field of Classification Search
USPC ......... 606/60, 62, 65, 73, 301, 304, 309, 321;
623/21.18, 17.11, 17.16; 411/393, 411,
411/412, 423, 424, 426
See application file for complete search history.

(56) References Cited

U.S. PATENT DOCUMENTS

| 3,726,180 | A | * | 4/1973 | Rosan, Sr. ...................... 411/422 |
| 4,450,591 | A |   | 5/1984 | Rappaport ........................ 3/1.9 |
| 5,360,450 | A | * | 11/1994 | Giannini ...................... 623/21.19 |
| 5,470,334 | A |   | 11/1995 | Ross et al. ........................ 606/72 |
| 5,607,304 | A | * | 3/1997 | Bailey et al. ..................... 433/174 |
| 5,683,460 | A | * | 11/1997 | Persoons ......................... 606/60 |
| 5,704,750 | A | * | 1/1998 | Bartos et al. .................... 411/411 |
| 5,816,812 | A |   | 10/1998 | Kownacki et al. ............. 433/174 |
| 5,897,593 | A | * | 4/1999 | Kohrs et al. .................. 623/17.16 |
| 5,951,560 | A | * | 9/1999 | Simon et al. ...................... 606/73 |
| 5,961,524 | A | * | 10/1999 | Crombie ......................... 606/104 |
| 5,964,768 | A | * | 10/1999 | Huebner ........................ 606/73 |
| 6,096,081 | A | * | 8/2000 | Grivas et al. ................. 623/17.11 |
| 6,168,631 | B1 |   | 1/2001 | Maxwell et al. ........... 623/21.18 |
| 6,264,677 | B1 | * | 7/2001 | Simon et al. ................... 606/232 |
| 6,436,139 | B1 | * | 8/2002 | Shapiro et al. .............. 623/17.11 |
| 6,503,252 | B2 | * | 1/2003 | Hansson ......................... 606/73 |
| 6,656,185 | B2 | * | 12/2003 | Gleason et al. ................. 606/74 |
| 7,608,105 | B2 | * | 10/2009 | Pavlov et al. .............. 623/17.11 |
| 2002/0038123 | A1 | * | 3/2002 | Visotsky et al. ................. 606/73 |
| 2002/0052608 | A1 | * | 5/2002 | Kvarnstrom et al. ......... 606/105 |
| 2002/0116066 | A1 | * | 8/2002 | Chauvin et al. ............ 623/17.16 |
| 2004/0097928 | A1 | * | 5/2004 | Zdeblick et al. ............... 606/61 |
| 2005/0177243 | A1 | * | 8/2005 | Lepow et al. .............. 623/21.11 |

FOREIGN PATENT DOCUMENTS

| DE | 10238091 | 2/2004 | .............. A61C 8/00 |
| EP | 0595782 | 10/1993 | ............... A61F 2/36 |
| EP | 0734703 | 3/1996 | ............... A61F 2/44 |
| FR | 2840799 | 6/2002 | ............. A61B 17/86 |
| WO | 9637169 | 5/1995 | ............... A61F 2/42 |
| WO | 0149200 | 7/2001 | |

OTHER PUBLICATIONS

PCT International Search Report and Written Opinion, PCT/US2005/001743, 16 pages, Mailing Date Aug. 4, 2005.

* cited by examiner

*Primary Examiner* — Thomas J Sweet
*Assistant Examiner* — Cheryl Miller
(74) *Attorney, Agent, or Firm* — Fulbright & Jaworski LLP

(57) ABSTRACT

A medical implant includes a body having a conical portion and adapted for implantation into a person's body. A plurality of threads formed around an exterior surface of the conical portion of the body are adapted to help secure the implant in place within the person's body.

27 Claims, 3 Drawing Sheets

CONICAL, THREADED SUBTALAR IMPLANT

TECHNICAL FIELD

This invention relates generally to biomedical implants and in particular to conical, threaded subtalar implants and methods for manufacturing the same.

BACKGROUND

Pes planus, or pes valgo planus, is a deformity producing a severe flat foot. The deformity occurs largely at one particular joint, the talocalcaneal articulation, which is the joint between the talus and calcaneus bones in the foot. There are typically three separate components of a valgus deformity at this joint: first, the calcaneus has a valgus position; second, the head of the talus angulates downward; and third, the forefoot is totally abducted in relation to the hindfoot. In addition, the Achilles tendon may be pulled laterally due to the outward rotation, or eversion, of the calcaneus.

Pes valgo planus often results from the failure of the arch to form in one or both feet of a child aged two to four, which is the typical age for the natural formation of the arch in the foot. The arch may fail to form due to loose joint connections or baby fat lodged between the foot bones of the child. Pes valgo planus also occurs in adults as a result of Posterior Tibial Tendon Dysfunction (PTTD), one of the more common tendon disorders involving the ankle. The posterior tibial tendon helps support the arch of the foot and provides power to point the foot down and to turn the foot inward. PTTD is typically caused by chronic inflammation, degenerative changes, and occasionally trauma, which lead to stretching, laxity, and eventual rupture of the posterior tibial tendon. People suffering from PTTD often experience tenderness and inflammation along the inner part of the ankle, and may experience weakness when standing on their toes. As the disease progresses, the person may experience loss of the arch of the foot while standing, and the foot tends to turn outward under weight. Late stages of the disease are associated with a flat foot deformity with degenerative changes in the joints below the ankle.

In many cases, the symptoms of pes valgo planus may be treated using conservative measures such as anti-inflammatory medications, rest, ice, shoe inserts or orthotic supports, or even ankle-foot braces. However, in some cases, such measures prove inadequate and the person may continue to experience severe foot or ankle pain or suffer from night cramps, pain when walking and/or standing, or lower back and knee pain. In such cases, a subtalar implant may be used to correct the flatfoot deformity while maintaining mobility of the subtalar joint. The subtalar implant is a small device that is inserted into a small opening in the talocalcaneal joint called the sinus tarsi. The placement of the implant restores the arch by preventing the displacement of the talus and by preventing the foot from rolling-in (pronating). In some cases, tissue may grow around the implant which helps hold the implant in place within the sinus tarsi.

SUMMARY OF THE INVENTION

The present invention provides a conical, threaded medical implant adapted for implantation within a person's body to limit motion in a joint having excessive mobility. In some embodiments, a medical implant includes a body having a conical portion and adapted for implantation into a person's body. A plurality of threads formed around an exterior surface of the conical portion of the body are adapted to help secure the implant in place within the person's body. In certain embodiments, the medical implant is a subtalar implant adapted for implantation into the person's body and sized to fit within a sinus tarsi of a subtalar joint in the person's body for at least partially preventing displacement of the talus. The plurality of threads may help secure the subtalar implant within the sinus tarsi.

Particular embodiments of the present invention may provide one or more advantages. For example, in certain embodiments in which the medical implant is adapted for use as a subtalar implant, the implant may be inserted via a subtalar arthroereisis operation into the sinus tarsi of a person suffering from pes valgo planus. Once inserted, the implant may reduce calcaneal eversion to a desirable level and block excessive displacement of the talus, thus correcting the pes valgo planus condition. In addition, the implant may allow normal motion of the subtalar joint while correcting the pes valgo planus, thus allowing the person to function normally.

Another advantage of certain embodiments is that at least a portion of the implant is tapered, or conical, to fit snugly within the tapered sinus tarsi. Thus, the likelihood of localized pressure points between the implant and the surrounding bones, which may cause pain or even result in the insert popping out of the sinus tarsi, is reduced as compared with prior implants. In addition, the insert may include threads that are sharp enough to help hold the insert in place within the person's sinus tarsi, yet dull enough to reduce the likelihood of the threads causing pain to the person as compared with prior implants. For example, in certain embodiments, the width of the crest of each thread may be wide enough to reduce or eliminate the likelihood of the threads causing pain.

Yet another advantage is that in certain embodiments, the implant includes one or more slots that increase the elasticity and resiliency of the implant. Thus, the implant may be better able to dissipate forces caused by impacts experienced by the implant, such as impacts caused by the person walking or running, for example.

Certain embodiments may provide all, some, or none of these advantages. Certain embodiments may provide one or more other advantages, one or more of which may be apparent to those skilled in the art from the figures, descriptions, and claims included herein.

BRIEF DESCRIPTION OF THE DRAWINGS

To provide a more complete understanding of the present invention and the features and advantages thereof, reference is made to the following description taken in conjunction with the accompanying drawings, in which.

DESCRIPTION OF EXAMPLE EMBODIMENTS

According to the present invention, a conical, threaded medical implant is adapted for implantation within a person's body to limit motion in a joint having excessive mobility. In certain embodiments, the medical implant is a subtalar implant adapted for implantation into the person's body and sized to fit within a sinus tarsi of a subtalar joint in the person's body for at least partially preventing displacement of the talus. However, it should be understood that various implants discussed herein may be otherwise used without departing from the scope of the invention.

Figure 1A:
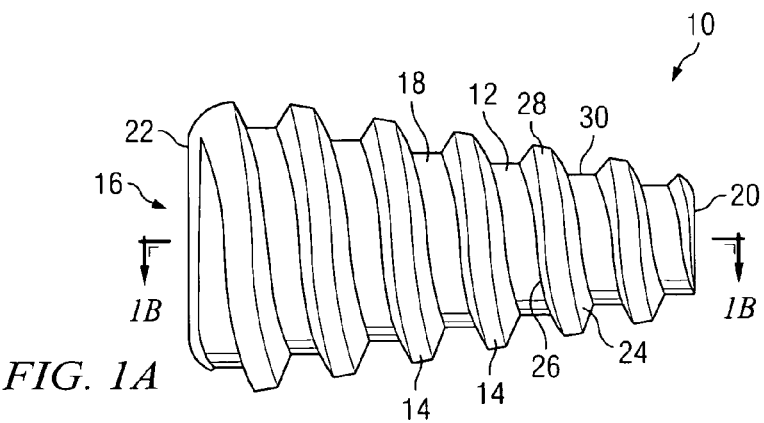
FIGS. 1A-1C illustrate a subtalar implant in accordance with one embodiment of the present invention.
Figure 1B:
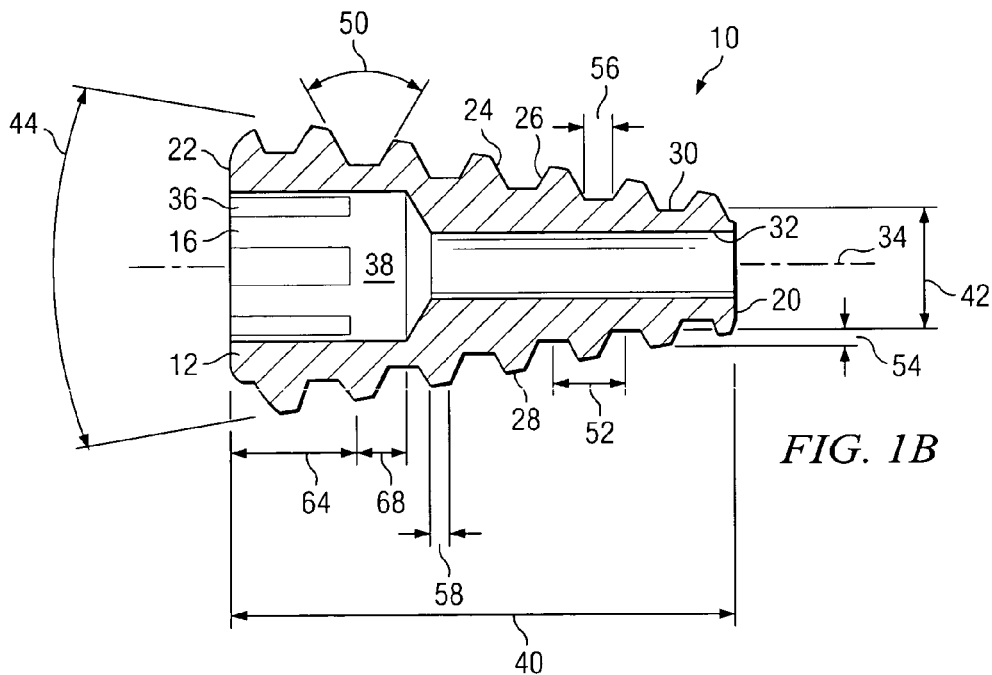
Figure 1C:
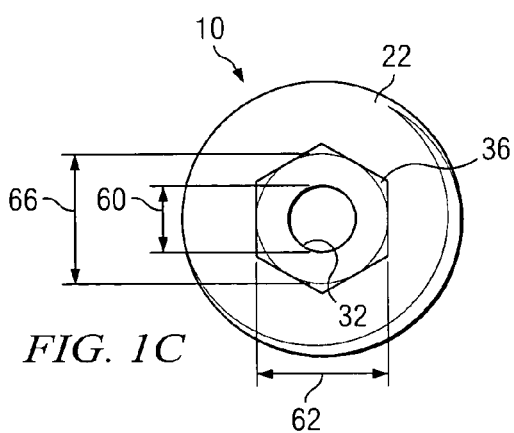

FIGS. 1A-1C illustrate a subtalar implant 10 in accordance with one embodiment of the present invention. In particular, FIG. 1A illustrates an external side view of implant 10, FIG. 1B illustrates a cross-sectional view of implant 10 taken along line A-A of FIG. 1A, and FIG. 1C illustrates an external end view of implant 10. In general, subtalar implant 10 may be inserted into the sinus tarsi of a person suffering from pes valgo planus in a subtalar arthroereisis operation. Once inserted, implant 10 may reduce calcaneal eversion and block excessive displacement of the talus, thus correcting the person's pes valgo planus. In addition, implant 10 may allow normal motion of the subtalar joint while correcting the pes valgo planus, thus allowing the person to function normally.

As shown in FIG. 1A, subtalar implant 10 includes a substantially conical body 12, a plurality of threads 14, and an engagement 16. Threads 14 are formed around the exterior surface 18 of body 12 and extend from a leading end 20 to a trailing end 22 of body 12. Threads 14 are provided to guide the insertion of implant 10 into, and to help secure implant 10 within, the sinus tarsi of a person. Each thread 14 includes a leading flank 24, a trailing flank 26, and a crest 28 connecting leading flank 24 with trailing flank 26. A root 30 is formed between each pair of adjacent threads 14 and connects the leading end 20 of one thread with the trailing end 22 of an adjacent thread 14.

As shown in FIG. 1B, engagement 16 is formed in trailing end 22 of body 12 and is coaxial with a bore 32 extending from leading end 22 of body 12 to engagement 16. Engagement 16 is adapted to receive and be engaged by an implantation tool such that implant 10 may be rotated about a longitudinal axis 34 for the implantation of implant 10 into the sinus tarsi. In this embodiment, engagement 16 comprises a recess having a hexagonal portion 36 integrated with a cylindrical portion 38 such that engagement 16 is adapted to receive and be engaged by a hex-head implantation tool, for example. In other embodiments, engagement 16 may comprise any other suitable types of recesses or other engagements adapted to receive or mate with other implantation tools. For example, engagement 16 may comprise a recess having a cruciform, rectangular, octagonal, or other shape.

FIG. 1B also illustrates various dimensions that define the shape of implant 10. For example, body 12 is at least partially defined by a length 40, a leading end diameter 42, and a taper angle 44. Threads 14 are at least partially defined by a thread angle 50, a pitch 52, a thread height 54, a root width 56, and a crest width 58. A variety of implants 10 may be formed in various sizes and having various values for the dimensions listed above. For example, length 40, leading end diameter 42, and taper angle 44 may be appropriately sized to fit within the sinus tarsi of a person. Since the sinus tarsi of different people may have a range of sizes, a variety of implants 10 may be provided having a range of lengths 40, leading end diameters 42, and taper angles 44 such that an appropriate implant 10 may be selected for each person based on the size and shape of that person's sinus tarsi. For example, for various implants 10, length 40 may range from approximatly 0.39 inches to approximately 0.78 inches and leading end diameter 42 may range from approximately 0.078 inches to approximately 0.39 inches. In the embodiment shown in FIGS. 1A-1C, length 40 is approximately 0.59 inches and leading end diameter 42 is approximately 0.163 inches.

Similarly, a range of taper angles 44 may be used in various implants 10 to correspond with a range of taper angles of the sinus tarsi of various people. For example, in a variety of implants 10, taper angle 44 may range from 10 to 30 degrees. In certain embodiments, taper angle 44 may range from approximately 15 to 20 degrees. In the embodiment shown in FIG. 1A-1C, taper angle 44 is approximately 18 degrees. By providing implants 10 having a range of taper angles 44, an implant 10 may be selected for a particular person that has a taper angle 44 substantially equal to the taper of the sinus tarsi of that person. Thus, implant 10 may fit more precisely or snugly within the tapered sinus tarsi as compared with prior cylindrical or other non-tapered implants. As a result, the likelihood of pressure points between implant 10 and the surrounding bones (including the talus and the calcaneus) which may cause pain or even result in insert 10 popping out of the sinus tarsi, is reduced as compared with prior cylindrical or other non-tapered implants.

The dimensions defining threads 14 may be selected based on a number of objectives, such as to provide implant 10 that may be easily threaded into the sinus tarsi and adequately secured in place within the sinus tarsi, and to limit or avoid pain to the patient, for example. In certain embodiments, threads 14 may be formed such that they are sharp enough to adequately secure implant 10 in place within a person's sinus tarsi, yet not sharp enough to cause pain to the person. In particular, the ratio of crest width 58 to one or more other thread dimensions, such as pitch 52 or thread height 54 for example, may be selected in order to provide these objectives. For example, the ratio of crest width 58 to pitch 52 may be greater than or approximately equal to 0.15. In certain embodiments, the ratio of crest width 58 to pitch 52 is between approximately 0.2 and 0.4. In the embodiment shown in FIGS. 1A-1C, the ratio of crest width 58 to pitch 52 is approximately 0.25. As another example, the ratio of crest width 58 to thread height 54 may be greater than or approximately equal to 0.3. In certain embodiments, the ratio of crest width 58 to thread height 54 is between approximately 0.5 and 1.0. In the embodiment shown in FIGS. 1A-1C, the ratio of crest width 58 to thread height 54 is approximately 0.72.

Figure 4:
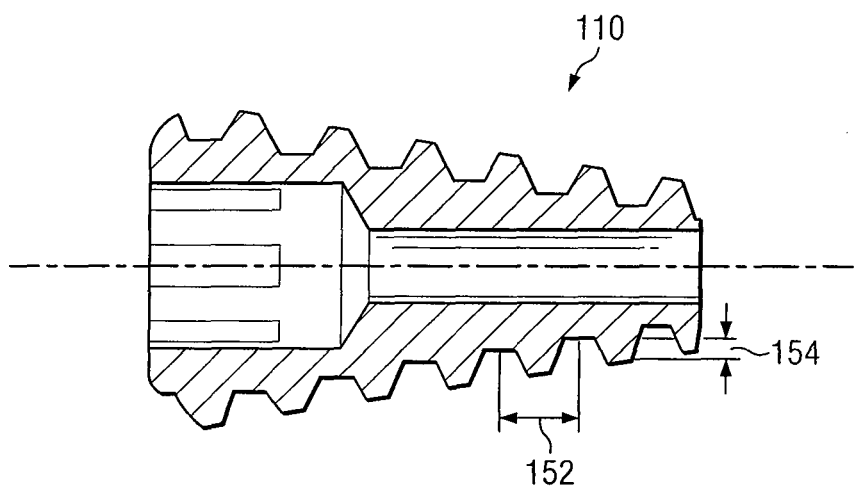
FIG. 4 illustrates an embodiment of a subtalar implant in accordance with a particular embodiment of the present disclosure.

Other dimensions of threads 14 may similarly be selected based on various objectives of insert 10, such as those discussed above. For example, thread angle 50 may be between approximately 45 and 75 degrees. In the embodiment shown in FIGS. 1A-1C, thread angle 50 is approximately 60 degrees. As another example, pitch 52 may be between approximately 0.050 and 0.200 inches. In certain embodiments, pitch 52 is between approximately 0.080 and 0.120 inches. In the embodiment shown in FIGS. 1A-1C, pitch 52 is approximately 0.090 inches. In certain other embodiments, pitch 52 is approximately 0.100 inches. As yet another example, thread height 54 may be between approximately 0.010 and 0.060 inches. In certain embodiments, thread height 54 is between approximately 0.020 and 0.050 inches. In the embodiment shown in FIGS. 1A-1C, thread height 54 is approximately 0.032 inches. In certain other embodiments, thread height 54 is approximately 0.041 inches. As yet another example, root width 56 may be between approximately 0.020 and 0.040inches. In the embodiment shown in FIGS. 1A-1C, root width 56 is approximately 0.030inches. In particular embodiments, an implant 110 may have a substantially constant thread height 154 and a substantially constant pitch 152 as illustrated, for example, in FIG. 4.

Taken together, FIGS. 1B and 1C illustrate engagement 16 and bore 32 formed in body 12 of implant 10. Bore 32 is at least partially defined by a bore diameter 60. Hexagonal portion 36 of engagement 16 is defined by a width 62 and depth 64 and cylindrical portion 38 engagement 16 is defined by a diameter 66 and depth 68. In the embodiment shown in FIGS. 1A-1C, hexagonal portion 36 has a width 62 and depth 64 of approximately 0.159 inches and 0.15 inches, respectively, while cylindrical portion 38 has a diameter 66 and depth 68 of approximately 0.166 inches and 0.20 inches, respectively. As shown in FIG. 1C, bore 32 has a diameter between 0.067 and 0.072 inches.

Implant 10 may be formed from any one or more materials suitable for forming medical implants, such as materials that have high strength-to-weight ratios and that are inert to human body fluids. In certain embodiments, implant 10 is formed from one or more titanium alloys, which provide several benefits. For example, titanium alloys are relatively lightweight, provide adequate strength for withstanding forces typically experienced by an implanted medical implant, are inert to human body fluids, and are visible in radiographs of the implant region. In particular embodiment, implant 10 is formed from the titanium based alloy Ti6Al4V ELI (per ASTM F136), which provides a desirable combination of benefits, such as those discussed above. In certain other embodiments, implant 10 is formed from one or more resorbable polymers, such as polylactides, polyglycolide, glycolide/lactide copolymers or other copolymers for example, or one or more implantable plastics, such as polyethylene or acetal copolymers for example.

Figure 2:
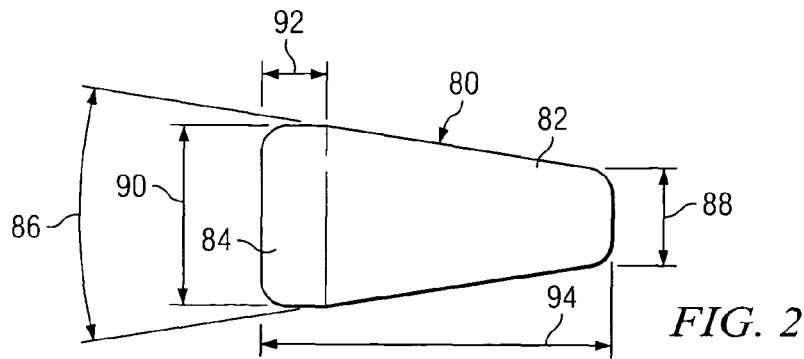
FIG. 2 illustrates a detail of an example slug used to form the implant shown in FIGS. 1A-1C.

FIG. 2 illustrates a detail of a slug 80 used to form implant 10 according to one embodiment of the present invention. In particular, threads 14 are formed in slug 80 to form implant 10 shown in FIGS. 1A-1C. As shown in FIG. 1, slug 80 includes a conical portion 82 and a cylindrical portion 84. Cylindrical portion 84 may be provided for the machining of implant 10. For example, cylindrical portion 84 of slug 80 may be gripped by various machining tools during the machining of slug 80 to form implant 10.

Slug 80 is at least partially defined by a taper angle 86, a leading end diameter 88, a cylindrical portion diameter 90, a cylindrical portion length 92, and an overall length 94. In the embodiment shown in FIG. 2 that is used to form implant 10 shown in FIGS. 1A-1C, taper angle 86 is approximately 18 degrees, leading end diameter 88 is approximately 0.163 inches, cylindrical portion diameter 90 is approximately 0.315 inches, cylindrical portion length 92 is approximately 0.110 inches, and overall length 94 is approximately 0.59 inches.

Figure 3A:
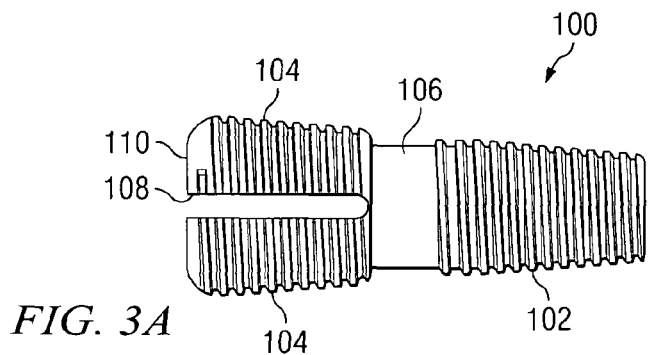
FIGS. 3A-3C illustrate various subtalar implants according to other embodiments of the present invention.
Figure 3B:
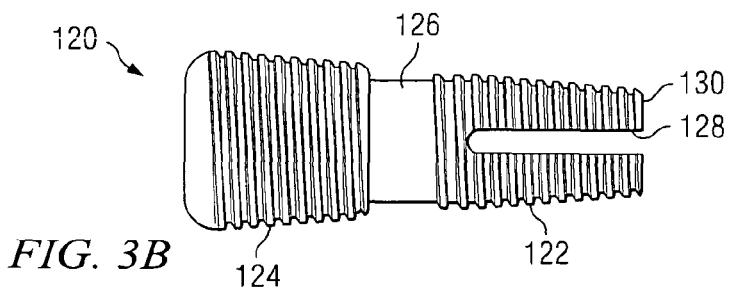
Figure 3C:
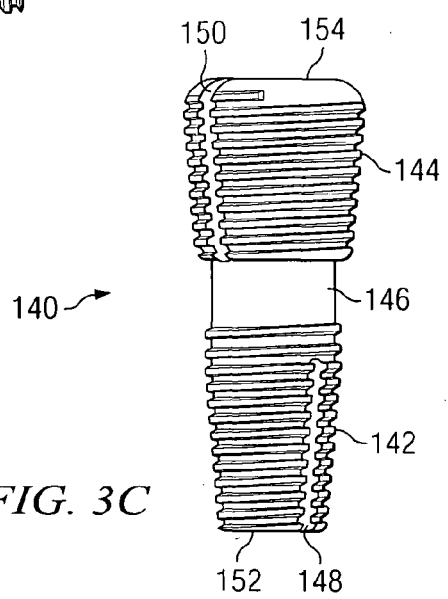

FIGS. 3A-3C illustrate various subtalar implants according to other embodiments of the present invention. As shown in FIG. 3A, implant 100 includes a leading conical portion 102, a trailing conical portion 104, and a cylindrical portion 106 connecting leading conical portion 102 with trailing conical portion 104. Cylindrical portion 106 may be used to hold implant 100 during the machining of implant 100. Implant 100 also includes a slot 108 extending across the diameter of trailing conical portion 104 and extending from a trailing end 110 of implant 100 substantially or completely through the length of trailing conical portion 104. Slot 108 may provide increased elasticity and resiliency to implant 100, which may reduce the likelihood of structural failure of implant 100 when subjected to various forces and stresses associated with being implanted in a person's sinus tarsi. For example, slots 108 may dissipate a portion of various impact forces experienced by implant 100, such as impact forces caused by the person walking or running.

As shown in FIG. 3B, implant 120 includes a leading conical portion 122, a trailing conical portion 124, a cylindrical portion 126 connecting leading conical portion 122 with trailing conical portion 124, and a slot 128. However, unlike slot 108 of implant 100, slot 128 of implant 120 extends across the diameter of leading conical portion 122 and extends from a leading end 130 of implant 120 substantially or completely through the length of leading conical portion 122. As discussed above regarding slot 108 of implant 100, slot 128 of implant 120 may provide increased elasticity to implant 120, which may reduce the likelihood of structural failure of implant 120 when subjected to various forces and stresses associated with being implanted in a person's sinus tarsi.

As shown in FIG. 3C, implant 140 includes a leading conical portion 142, a trailing conical portion 144, a cylindrical portion 146 connecting leading conical portion 142 with trailing conical portion 144, a first slot 148, and a second slot 150. First slot 148 extends across the diameter of leading conical portion 142 and extends from a leading end 152 of implant 140 substantially or completely through the length of leading conical portion 142. Second slot 150 extends across the diameter of trailing conical portion 144 and extends from a trailing end 154 of implant 140 substantially or completely through the length of trailing conical portion 144. In the embodiment shown in FIG. 3C, first slot 148 and second slot 150 are formed substantially perpendicular to one another. As discussed above regarding slots 108 and 128, slots 148 and 150 of implant 140 may provide increased elasticity to implant 140, which may reduce the likelihood of structural failure of implant 140 when subjected to various forces and stresses associated with being implanted in a person's sinus tarsi.

Although the present invention has been described with several embodiments, a number of changes, substitutions, variations, alterations, and modifications may be suggested to one skilled in the art, and it is intended that the invention encompass all such changes, substitutions, variations, alterations, and modifications as fall within the spirit and scope of the appended claims.

What is claimed is:

1. A medical implant, comprising:
a headless body configured to fit snugly into a sinus tarsi of a subtalar joint in a human foot, the body comprising:
a first end having a first diameter;
a second end having a second diameter;
at least one continuous and uninterrupted thread including a crest with a substantially flat surface and having a substantially constant thread height and helically traversing a length of an exterior surface of the body, the length spanning from the first end to the second end;
a recessed engagement in the first end; and wherein:
a circumference of the exterior surface tapers from the first diameter to the second diameter along the length of the body; and
the thread includes a leading flank spanning from the crest to a thread root and a trailing flank spanning from the crest to the thread root, the leading flank separated from the trailing flank by a narrowing clearance therebetween.

2. The medical implant of claim 1, wherein:
the circumference of the exterior surface tapers uniformly from the first end to the second end according to a predetermined taper angle;
the leading flank and the trailing flank define a constant thread angle therebetween; and
the direction of incline of the leading flank is opposite the direction of incline of the trailing flank.

3. The medical implant of claim 2, wherein the recessed engagement comprises:
a hexagonal portion;

a cylindrical portion; and
a countersink portion.

4. The medical implant of claim 2, wherein the taper angle measures between 15 degrees and 20 degrees.

5. The medical implant of claim 2, wherein:
the at least one thread has a substantially constant pitch;
the at least one thread further includes a crest width;
the ratio of the crest width to the thread height is at least 0.3;
the thread angle measures approximately 60 degrees; and further comprising:
a thread root width measuring between 0.020 inches and 0.040 inches.

6. The medical implant of claim 2, wherein:
the first end comprises a first flat face encircling the recessed engagement; and
the second end comprises a second flat face encircling a bore.

7. The medical implant of claim 2, wherein the at least one thread further includes a crest width and a substantially constant pitch, wherein the ratio of the crest width to the pitch is between 0.25 and 0.4.

8. The medical implant of claim 2, wherein the at least one thread further includes a thread root width measuring between 0.020 inches and 0.040 inches.

9. The medical implant of claim 2, wherein:
the body is generally conical; and
the circumference of the exterior surface comprises the crest of the thread.

10. The medical implant of claim 2, wherein:
the taper angle measures approximately 18 degrees;
the thread height is approximately 0.032 inches;
a root width of the thread is approximately 0.030 inches; and
a pitch of the thread is approximately 0.090 inches.

11. The medical implant of claim 2, wherein:
the thread is configured to secure the body into the sinus tarsi, and to limit pain caused to a patient by the thread once the medical implant is inserted into the sinus tarsi;
the body is configured to:
reduce calcaneal eversion;
at least partially prevent displacement of a talus without penetrating bone; and
limit pain caused by localized pressure points between the body and one or more surrounding bones once the medical implant is inserted into the sinus tarsi.

12. The medical implant of claim 2, wherein:
the entirety of the medical device is adapted for insertion into the sinus tarsi and, once inserted is operable to minimize pressure points between the body and a talus bone and the body and a calcaneus bone when the medical device is implanted into the sinus tarsi.

13. The medical implant of claim 2, further comprising a bore coaxial with the recessed engagement and extending from the recessed engagement to the second end.

14. The medical implant of claim 2, wherein the direction of incline of the leading flank is equal and opposite to the direction of incline of the trailing flank.

15. A medical implant, comprising:
a body configured to fit snugly into a sinus tarsi of a subtalar joint in a human foot, the body comprising:
a first end having a first diameter;
a second end having a second diameter;
a recessed engagement in the first end;
a bore coaxial with the recessed engagement and extending from the recessed engagement to the second end;
at least one continuous and uninterrupted thread including:
a crest with a substantially flat surface and having a substantially constant thread height and helically traversing a length of an exterior surface of the body, the length spanning from the first end to the second end; and
a leading flank spanning from the crest to a thread root and a trailing flank spanning from the crest to the thread root, the leading flank separated from the trailing flank by a narrowing clearance therebetween, the leading flank and the trailing flank defining a thread angle; and wherein
a circumference of the exterior surface tapers from the first diameter to the second diameter along the length of the body; and
the thread is configured to secure the body into the sinus tarsi, and to minimize pain caused to a patient by the thread once the body is inserted into the sinus tarsi.

16. The medical implant of claim 15, wherein the body is unperforated along its length.

17. A medical implant, comprising:
a body adapted for implantation into a sinus tarsi of a subtalar joint in a human foot, the body comprising:
a first end having a first diameter;
a second end having a second diameter;
at least one continuous and uninterrupted thread including a crest with a substantially flat surface and having a substantially constant thread height and helically traversing a length of an exterior surface of the body, the length spanning from the first end to the second end; and
a recessed engagement in the first end, the recessed engagement comprising:
a hexagonal portion;
a cylindrical portion;
a countersink portion; and wherein:
a circumference of the exterior surface tapers from the first diameter to the second diameter along the length of the body;
the taper angle is configured to minimize pressure points between the body and a talus bone and the body and a calcaneus bone when the body is implanted into the sinus tarsi; and
the thread includes a leading flank spanning from the crest to a thread root and a trailing flank spanning from the crest to the thread root, the leading flank separated from the trailing flank by a narrowing clearance therebetween.

18. A method of forming a medical implant, comprising:
configuring a headless body to fit snugly into a sinus tarsi of a subtalar joint in a human foot, the body comprising:
a first end having a first diameter;
a second end having a second diameter;
forming at least one continuous and uninterrupted thread including a crest with a substantially flat surface and having a substantially constant thread height and helically traversing a length of an exterior surface of the body, the length spanning from the first end to the second end;
forming a recessed engagement in the first end; and wherein:
a circumference of the exterior surface tapers from the first diameter to the second diameter along the length of the body; and
the thread includes a leading flank spanning from the crest to a thread root and a trailing flank spanning from the crest to the thread root, the leading flank separated from the trailing flank by a narrowing clearance therebetween.

19. The method of claim 18, wherein:
the circumference of the exterior surface tapers uniformly from the first end to the second end according to a predetermined taper angle;
the leading flank and the trailing flank define a constant thread angle therebetween; and
the direction of incline of the leading flank is opposite the direction of incline of the trailing flank.

20. The method of claim 19, wherein the recessed engagement comprises:
a hexagonal portion;
a cylindrical portion; and
a countersink portion.

21. The method of claim 19, wherein:
the first end comprises:
a first flat face; and
the second end comprises a second flat face.

22. The method of claim 19, further comprising forming a bore coaxial with the recessed engagement and extending from the recessed engagement to the second end.

23. The method of claim 19, wherein the at least one thread further includes:
the thread angle measuring approximately 60 degrees;
a crest width, wherein the ratio of the crest width to the thread height is at least 0.3; and
a thread root width measuring between 0.020 inches and 0.040 inches.

24. The method of claim 19, wherein:
the body is generally conical; and
the circumference of the exterior surface comprises the crest of the thread.

25. A method, comprising:
inserting into the sinus tarsi:
a body configured to fit snugly into a sinus tarsi of a subtalar joint in a human foot, the body comprising:
a first end having a first diameter;
a second end having a second diameter;
a recessed engagement in the first end;
a bore coaxial with the recessed engagement and extending from the recessed engagement to the second end;
at least one continuous and uninterrupted thread including:
a crest with a substantially flat surface and having a substantially constant thread height and helically traversing a length of an exterior surface of the body, the length spanning from the first end to the second end; and
a leading flank inclined away from the second end and spanning from the crest to a thread root and a trailing flank inclined away from the first end and spanning from the crest to the thread root, the leading flank and the trailing flank defining a thread angle; and wherein
a circumference of the exterior surface tapers from the first diameter to the second diameter along the length of the body; and
the thread is configured to secure the body into the sinus tarsi, and to limit pain caused to a patient by the thread once the body is inserted into the sinus tarsi.

26. The method of claim 25, wherein:
the circumference of the exterior surface tapers uniformly from the first end to the second end according to a first taper angle; the first taper angle defined by a second taper angle of the sinus tarsi of the second human foot.

27. The method of claim 25, wherein the entirety of the medical device is inserted into the sinus tarsi.

\* \* \* \* \*